(12) United States Patent
Huang et al.

(10) Patent No.: US 7,658,947 B2
(45) Date of Patent: Feb. 9, 2010

(54) THERMO-GELLING COMPOSITION

(75) Inventors: Yanbin Huang, Roswell, GA (US);
Shu-Ping Yang, Alpharetta, GA (US);
Sharon Linda Greene, Canton, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 845 days.

(21) Appl. No.: 10/877,855

(22) Filed: Jun. 25, 2004

(65) Prior Publication Data

US 2005/0287087 A1  Dec. 29, 2005

(51) Int. Cl.
*A61K 9/14* (2006.01)
(52) U.S. Cl. ..................................................... 424/488
(58) Field of Classification Search ................... None
See application file for complete search history.

(56) References Cited

U.S. PATENT DOCUMENTS

| | | | | |
|---|---|---|---|---|
| 3,879,369 | A | * | 4/1975 | Nolan ......................... 530/413 |
| 4,140,763 | A | | 2/1979 | Bachrach et al. |
| 5,624,962 | A | | 4/1997 | Takeuchi et al. |
| 5,985,299 | A | * | 11/1999 | Buerger et al. ............... 424/402 |
| 6,319,984 | B1 | | 11/2001 | Song et al. |

FOREIGN PATENT DOCUMENTS

| | | |
|---|---|---|
| EP | 0177893 A2 | 4/1986 |
| EP | 0286791 A1 | 10/1988 |
| EP | 0694310 A1 | 1/1996 |
| EP | 0782850 A1 | 7/1997 |

OTHER PUBLICATIONS

Alexandridis, P. et al., "Poly(ethylene oxide)-poly(propylene oxide)-poly(ethylene oxide) block copolymer surfactants in aqueous solutions and at interfaces: thermodynamics, structure, dynamics, and modeling", *Colloids and Surfaces A: Physicochemical and Engineering Aspects* 96, 1995, pp. 1-46.
Bromberg, L. E. et al., "Temperature-responsive gels and thermogelling polymer matrices for protein and peptide delivery", *Advances Drug Delivery Reviews*, 31, 1998, pp. 197-221.
Chenite, A. et al., "Rheological characterization of thermogelling chitosan/glycerol-phosphate solutions", *Carbohydrate Polymers*, 46, 2001, pp. 39-47.
Chenite, A. et al., "Novel injectable neutral solutions of chitosan form biodegradable gels in situ", *Biomaterials*, 21, 2000, pp. 2155-2161.
Dow Chemical Company, *Methocel Cellulose Ethers Technical Handbook*, Sep. 2002, pp. 1-29.
Durand, A. et al., "Thermogelation in Aqueous Polymer Solutions", *Stimuli-Responsive Water Soluble and Amphiphilic Polymers*, ACS, 2001, pp. 181-207.
Haider, M. et al., "Genetically engineered polymers: status and prospects for controlled release", *Journal of Controlled Release*, 95, 2004, pp. 1-26.
Iso, N. et al., "Effects of Sucrose and Citric Acid on the Sol-Gel Transformation of Methylcellulose in Water", *Agricultural and Biological Chemistry*, vol. 34, No. 12, 1970, pp. 1867-1869.
Jeong B. et al., "Thermosensitive sol-gel reversible hydrogels", *Advanced Drug Delivery Reviews*, 54, 2002, pp. 37-51.
Jeong, B. et al., "Lessons from nature: stimuli-responsive polymers and their biomedical applications", *Trends in Biotechnology*, vol. 20, No. 7, Jul. 2002, pp. 305-311.
Kissel, T. et al., "ABA-triblock copolymers from biodegradable polyester A-blocks and hydrophilic poly(ethylene oxide) B-blocks as a candidate for in situ forming hydrogel delivery system for proteins", *Advanced Drug Delivery Reviews*, 54, 2002, pp. 99-134.
Kobayashi, K. et al., "Thermoreversible Gelation of Aqueous Methylcellulose Solutions", *Macromolecules*, 32, 1999, pp. 7070-7077.
Kundu, P.P. et al., "Effects of salts and surfactants and their doses on the gelation of extremely dilute solutions of methyl cellulose", *Polymer*, 42, 2001, pp. 2015-2020.
Kundu, P.P. et al., "Effect of alcoholic, glycolic, and polyester resin additives on the gelation of dilute solution (1%) of methylcellulose", *Carbohydrate Polymers*, 51, 2003, pp. 57-61.
Takeuchi, M. et al., "Rheological properties of reversible thermosetting in situ gelling solutions with the methylcellulose-polyethylene glycol-citric acid ternary system", *Colloid and Polymer Science*, 281, 2003, pp. 1178-1183.
Xu, Y. et al., "Salt-Assisted and Salt-Suppressed Sol-Gel Transitions of Methylcellulose in Water", *Langmuir*, 20, 2004, pp. 646-652.

* cited by examiner

*Primary Examiner*—Eric E. Silverman
(74) *Attorney, Agent, or Firm*—James B. Robinson; Vincent T. Kung

(57) ABSTRACT

There is provided a new thermo-gelling composition made with methylcellulose and citric acid. This composition may also have an effective amount of a treating agent, which may be a medicinal agent, cosmetic agent, moisturizer, adjuvant, nutritional agent, other ingredients and combinations thereof. The composition is useful in delivering moisturizers or pharmaceutically active agents to the user in a controlled release manner through the mucosal tissues in a body cavity, or on body surfaces, or as a subcutaneously injected medicament. The composition may also be used as a replacement for the soft tissues of the body as in, for example, the foot cushion and cartilage repair.

19 Claims, 1 Drawing Sheet

Methylcellulose

Hydroxypropyl Methylcellulose

THERMO-GELLING COMPOSITION

BACKGROUND OF THE INVENTION

The present invention concerns the delivery of treating agents and moisturizers to the body as well as soft tissue replacement.

Often in the treatment of chronic conditions or illnesses, treating substances must be delivered to specific areas of the body and remain there for some time. The contact time is important to the efficacy of many treatments because they must be absorbed by the body or because they act slowly on the cause of the malady. Other factors to be considered in the choice of delivery system are ease of application, coverage, durability of effects, that it be leak resistant and comfortable, and that the system have the capability of delivering other treating agents over time in a controlled release manner.

Various methods have been used to increase the contact time of the treating substance with the body. Increasing the viscosity of the treating composition, for example, has been used for some time, but a high viscosity is sometimes an impediment to proper administration of the composition. A composition that is too viscous is difficult to work with and to put into place in the body. Multi-component compositions that react upon mixing to become semi-solid in place likewise suffer from the same problem; that of being difficult to administer. Multi-component compositions also can be quite complicated, sometimes having many ingredients in precise ratios which may pose a problem for the addition of treating agents.

While the current methods may solve some of the problems associated with the delivery of substances, they do not address all of the basic requirements of a successful system. There remains a need, therefore, for a delivery system that may be used by a consumer and which will be effective and easy to apply and that may be extended to deliver other treating agents.

SUMMARY OF THE INVENTION

In response to the discussed difficulties and problems encountered in the prior art, a new aqueous binary thermo-gelling composition made from methylcellulose and citric acid and salts thereof has been developed. More particularly, the thermo-gelling composition includes an aqueous base of water, methylcellulose and citric acid. The aqueous liquid may be water or a combination of water and other compatible liquids.

Temperature responsive or "thermo-gelling" compositions respond to temperature changes, in this case temperature increases, by changing from a liquid to a gel at about mammalian body temperatures.

This composition may further have an effective amount of a treating agent which may be a medical (pharmaceutically active) or cosmetic agent or nutritional agent or combinations thereof. Exemplary medicaments include, but are not limited to, agents for treating infections and menstruation disorders, agents for treating cardiovascular conditions, agents for treating internal conditions, agents for treating mental health conditions, anti-inflammatory agents, chemotherapeutic agents, cardiac tonics, expectorants, oral antiseptics, enzymes, birth control agents, ophthalmic treating agents and combinations thereof. Cosmetic agents include sunscreens, acne treatments, and skin softeners while nutritional agents include vitamins and minerals.

The composition can be delivered to body cavities following routes such as oral, ophthalmic, nasal, rectal, and vaginal routes. It may also be delivered to body surfaces as topical and transdermal drug carriers. The composition may likewise be delivered subcutaneously or intra-muscularly.

It has been found that a soft tissue replacement may also be configured from the aqueous composition methylcellulose and citric acid and salts thereof.

DETAILED DESCRIPTION OF THE INVENTION

Figure 1:
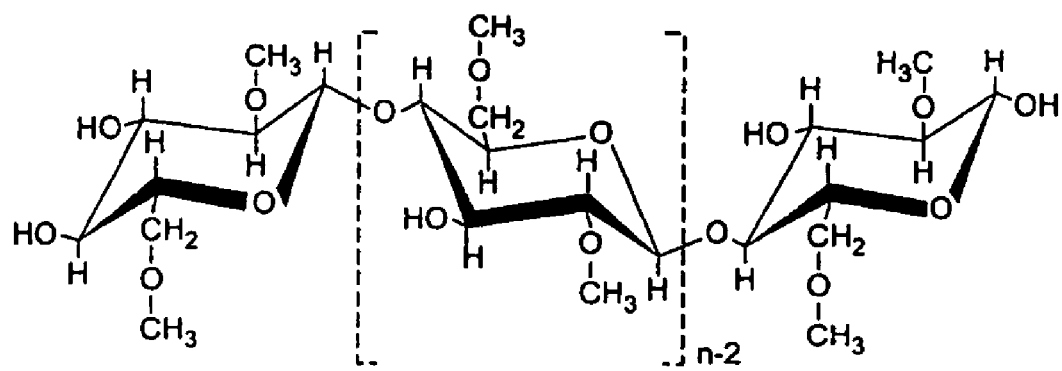
FIG. 1 is a depiction of methylcellulose

The delivery of treating agents such as medicaments, nutritional agents and moisturizers to parts of the body is important for comfort and medical reasons. Current systems, as described above, have not entirely met the needs of users. The inventors have found a novel composition which is simple, easy to apply and that may be used to deliver other agents. Because the compositions of this invention are long lasting, they allow for the controlled release of additional treating agents. The release of the active agent over a period of time, is an important requirement for many effective treatments.

The composition of the invention, though primarily directed toward use with the human body, may also be used in veterinary applications, particularly for mammals. The application of the invention to animals will, of course, require modification of the amounts of ingredients to compensate for different body temperatures and will also require tailoring the amounts of any additional ingredients so that they will be effective. Dogs, for example, have a normal body temperature of about 38.5° C. Such modification is within the contemplated scope of the invention and within the ability of those skilled in the art.

This invention is concerned with the gelling of the inventive composition in response to temperature, i.e., thermo-gelling, rather than other factors, since it is a more general characteristic than others, (i.e.; it doesn't vary as greatly throughout the typical mammalian body as do pH and ionic composition). As used herein, the term "gel" is defined as a colloid in which a disperse phase has combined with a continuous phase to produce a viscous, jelly-like product. Generally speaking, the disperse phase will be a solid and the continuous phase will be an aqueous liquid. The gels formed according to the present invention may be relatively "stiff" and can be characterized as a semisolid containing a certain quantity of water. A colloidal solution with water is often also called a "hydro-sol".

As used herein, the term "themo-gel" or "thermo-gelling" refers to a colloidal system that responds to temperature changes by changing from a liquid to a gel. For purposes of the present invention, the "thermo-gel" refers to colloidal systems that change from a liquid to a gel upon an increase in temperature. The colloidal systems of the present invention are different from more well known colloidal systems that change from a liquid to a gel upon a decrease in temperature.

The system of this invention uses a thermo-gelling composition that includes a base of water, methylcellulose or hydroxypropyl methylcellulose (hereinafter referred to collectively as methylcellulose) and citric acid and salts thereof. Desirably, the aqueous liquid is de-ionized water. It is contemplated that water may be combined with small amounts of other compatible liquids such as, for example, glycerin. The thermo-gelling composition is a suitable base to which may be added various "treating agents" which may be medicinal agents, cosmetic agents, nutritional agents, adjuvants, moisturizers and other ingredients as desired without appreciably changing the gelling properties of the base. The resulting therapeutic compositions have a wide range of uses and applications.

As noted above, temperature responsive or thermo-gelling solutions respond to temperature changes, in this case temperature increases, by changing from a liquid to a gel. The temperature range of interest for the invention is between about 25 and 40° C., more particularly between about 35 and 39° C. or still more particularly around that of the human body (37° C.). Compositions that change state at about this temperature are useful because they will remain in a body cavity, for example, after they have been delivered. A liquid would have difficulty in remaining in place in many locations of the body, particular with movement of the individual.

Therapeutic compositions containing the thermo-gelling base of the invention may be used on any mucosal surface location of the body such as in vaginal, rectal, oral cavity, ophthalmic and nasal locations. It may also be used a topical and transdermal composition and as an injectable in-situ gelling composition for subcutaneous or intramuscular applications to deliver specific medicaments where needed.

In the case of injectable applications, after injection, the thermo-gelling composition along with the active ingredients becomes a semisolid gel and forms a drug "reservoir" in contact with body fluid and so enables the sustained release of the active ingredients. This approach helps to lower the injection frequency and hence improves patient compliance, which is especially important for drugs currently only available through injection. This includes drugs such as protein/peptide (e.g. insulin and growth hormones) drugs, for example.

It has also been found that the thermo-gelling composition may be used as a soft tissue replacement in, for example, foot cushions, articular cartilage, and wound dressings. In these applications, the thermo-gelling composition is applied as a liquid to minimize disturbance to the site and to accommodate the configuration of the target site. It then solidifies in situ to provide mechanical support and barrier functionality.

Figure 2:
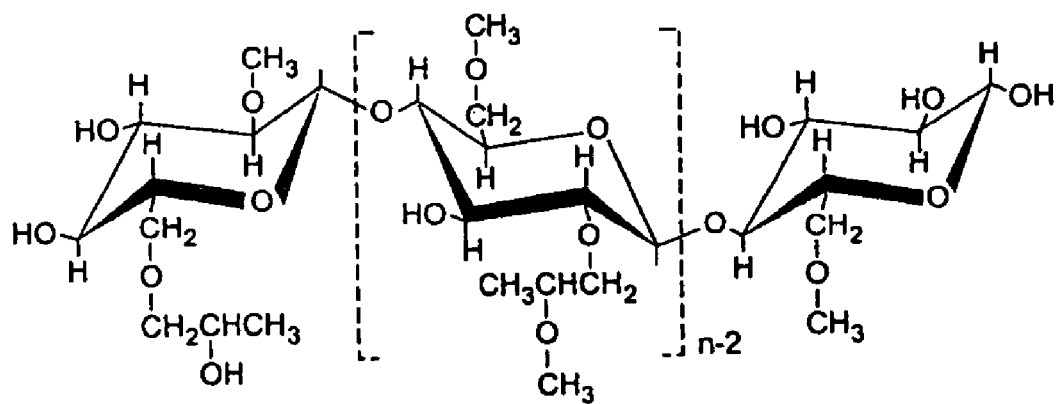
FIG. 2 is a depiction of hydroxypropyl methylcellulose.

Methylcellulose (FIG. 1) and hydroxypropyl methylcellulose (FIG. 2) have a polymeric backbone made of cellulose, a natural carbohydrate that contains a basic repeating structure of anhydroglucose units. These polymers are commercially available from a number of sources including the Dow Chemical Company of Midland, Mich. The inventors have found that the molecular weight of the methylcellulose is important to the success of the composition, particularly that it be relatively low, i.e., producing a viscosity for a 2 weight percent water solution which should be less than 1000 mPa·s at 20° C. Methylcellulose concentration should be relatively high, i.e., between 0.5 and 10 weight percent.

A solution of methylcellulose may be made in cold water (about room temperature or below) by simply mixing the desired amount of methylcellulose in water with mild agitation. Alternatively, the methylcellulose may be first dispersed in hot water (about 50-90° C.), and cold water added to the suspension to dissolve the methylcellulose.

Citric acid (2-hyroxy, 1, 2, 3 propanetricarboxylic acid) is colorless, odorless and acidic tasting. Citric acid is also commercially available from numerous manufacturers. Citric acid can be in its acid form (hydrate or anhydrate) or salt form (e.g. sodium potassium salts).

It is desired that the thermo-gelling composition of this invention have from a positive amount to about 6 weight percent of citric acid and salts thereof and from about 0.5 to 10 weight percent of methylcellulose with the balance water (preferably de-ionized) as a base. Any optional medicaments, moisturizers and other ingredients may be added as desired. More particularly the citric acid and salts thereof can be present in an amount between a 0.5 and 3 weight percent and the methylcellulose in an amount between about 2 and 7 weight percent with the balance water and any medicaments and/or moisturizers. The final composition should have a pH ranging from 2 to 9.

The additional treating agents mentioned above include active agents and medicaments selected generally from the classes of medicinal agents, (i.e., pharmaceutically active agents), cosmetic agents, moisturizers, adjuvants and nutritional agents, as well as other desirable ingredients. The treating agent may be used singly or as a mixture of two or more such agents.

Exemplary medicinal agents include agents for treating infections such as antibacterial, anti-fungal and antibiotic agents; for treating cardiovascular conditions such as chlorothiazide (diuretic), propranolol (antihypertensive), hydralazine (peripheral vasodilator), isosorbide or nitroglycerin (coronary vasodilators), metoprolol (beta blocker), procainamide (antiarrythmic), clofibrate (cholesterol reducer) or coumadin (anticoagulant); agents for treating internal conditions such as conjugated estrogen (hormone), tolbutamide (antidiabetic), levothyroxine (thyroid conditions), propantheline (antispasmodic), cimetidine (antacid), phenyl propanolamine (anti-obesity), atropine or diphenoxalate (anti-diarrheal agents), docusate (laxative), or prochlorperazine (antinauseant); agents for treating mental health conditions such as haloperidol or chlorpromazine (tranquilizers), doxepin (psychostimulant), phenytoin (anticonvulsant), levo dopa (anti-parkinism), benzodiazepine (anti-anxiety) or phenobarbital (sedative); anti-inflammatory agents such as fluorometholone, acetaminophen, phenacetin, aspirin, hydrocortisone, or predisone; anti-histamines such as diphenhydramine hydrochloride or dexchlorpheniramine maleate; antibiotics such as sulfanilamide, sulfamethizole, tetracycline hydrochloride, penicillin and its derivatives, cephalosporin derivatives or erythromycin; chemotherapeutic agents such as sulfathiazole, doxorubicin, cisplatin or nitrofurazone; topical anaesthetics such as benzocaine; cardiac tonics such as digitalis or digoxin; antitussives and expectorants such as codeine phosphate, dextromethorphan or isoproterenol hydrochloride; oral antiseptics such as chlor hexidine hydrochloride or hexylresorcinol; enzymes such as lysozyme hydrochloride or dextronase; birth control agents such as estrogen; ophthalmic treating agents such as timolol or gentamycin, and the like. In addition, medicinal treating agents may also include whole proteins such as the VP3 capsid protein (also known as the VPThr and VP1 capsid proteins in other nomenclature systems) as described in U.S. Pat. No. 4,140,763, insulin or interferon; polypeptide treating agents such as endorphins, human growth hormone, or bovine growth hormone, or still lower molecular weight polypeptides or conjugates of those polypeptides linked protein carriers.

Exemplary cosmetic agents include sunscreens such as p-dimethylaminobenzoic acid or glyceryl p-aminobenzoate, a skin softener such as urea, keratolytic agents such as salicylic acid; acne treating agents such as benzoyl peroxide or sulfur; perfumes, and the like.

The composition can be used as a moisturizing formulation with or without out pharmaceutically active ingredients. Suitable moisturizers are known in the art and include vitamin E, aloe, glycerin, propylene glycol, alpha-hydroxy acid.

One or more adjuvants may also be included with another treating agent, and when so used, an adjuvant is included in the meaning of the phrase "treating agent" as that phrase is used herein. Exemplary of useful adjuvants are chelating agents such as ethylenediaminetetracetic acid (EDTA) that bind calcium ions and assist in passage of medicinal agents through the mucosa and into the blood stream.

Nutritional agents such as vitamins and/or minerals like riboflavin and iron, respectively, and combinations thereof may also comprise useful treating agents herein.

The composition can also include effective amounts of other desirable ingredients (other than methylcellulose, citric acid, and other active ingredients) including pH adjusting acids/bases, e.g. hydrochloric acid or sodium hydroxide, tonicity adjusters, e.g. sodium chloride and mannitol, preservatives, e.g. parabens, benzoic acid, and benzalkonium chloride, antioxidants, e.g. ascorbic acid, and polymeric thickeners/viscosity adjusters, e.g., alginate and chitosan and combinations thereof. If present, these are generally effective in amounts from a positive amount to about 5 weight percent.

The treating agent or medicament is present in the compositions of this invention in an amount that is sufficient to prevent, cure and/or treat a condition for a desired period of time for which the composition of this invention is to be administered, and such an amount is referred to herein as "an effective amount". As is well known, particularly in the medicinal arts, effective amounts of medicinal agents vary with the particular agent employed, the condition being treated and the rate at which the composition containing the medicinal agent is eliminated from the body, as well as varying with the species in which it is used, and the body weight of that individual. Consequently, effective amounts of treating agents may not be defined for each agent. Thus, an effective amount is that amount which in a composition of this invention provides a sufficient amount of the treating agent to provide the requisite activity of treating agent in or on the body of the treated individual for the desired period of time, and is typically less than that amount usually used.

Since amounts of particular treating agents in the blood stream that are suitable for treating particular conditions are generally known, as are suitable amounts of treating agents used in cosmetics, it is a relatively easy laboratory task to formulate a series of controlled release compositions of this invention containing a range of such treating agents to determine the effective amount of such a treating agent for a particular composition. While the effective amount for all treating agents cannot be stated, typical compositions of this invention may contain about one microgram to about one gram of treating agent per dose administered.

The following embodiments illustrate the invention in varying scope. All the following example formulations were tested for their thermogelation property by the inverting-flow test method. In this test method, glass vials (about 12.7 mm diameter) containing the formulations are maintained at a given temperature for a specific time period, and are then inverted to see the flow behavior. A gel was defined as systems without notable flow by this method.

EXAMPLE 1

Aqueous solutions of 10 weight percent METHOCEL A15LV methylcellulose (Dow Chemical) in de-ionized water were prepared using the hot/cold technique described above. METHOCEL A15LV methylcellulose has a viscosity of 15 mPa·s measured at 2 weight percent concentration in water at 20 C. A 15 weight percent citric acid solution was prepared by mixing 15.8 grams citric acid and 4.3 grams sodium hydroxide into 85 ml de-ionized water at room temperature. These stock solutions were used in the following examples at varying amounts.

The specific solutions were made by mixing the desired amount of the two solutions and then diluting with de-ionized water. The solutions were then kept overnight (about 18 hours) at 4° C., then placed in another area at room temperature for 1 hour and finally placed in an oven at 37° C. The samples (about 1 ml) were in glass vials in the oven for 30 minutes (Table 1) and 2 hours (Table 2) and then inverted in the oven for two minutes as described above. The results are given in Tables 1 and 2 where the methylcellulose concentration (MC %) is given horizontally across the bottom of each table (X-axis), the citric acid concentration is given in the first vertical column (Y-axis) and the result is in the box at the intersection of the desired solution. As used in the following Tables, the term "gel" means the solution remained inverted for at least two minutes without running and the term "not" means the solution did not gel sufficiently to pass the inverting-flow test.

TABLE 1

| Citric | | | acid % | | | | |
|---|---|---|---|---|---|---|---|
| 4% | Gel | Gel | Gel | Gel | | | |
| 3% | Gel | Gel | Gel | Gel | | | |
| 2% | Not | | Gel | | | | |
| 1% | Not | Not | Gel | | | | |
| 0.5% | Not | Not | Gel | | | | |
| 0.3% | | Not | Not | | | | |
| 0.1% | | Not | Not | | | | |
| 0 | | Not | Not | Not | Gel | Gel | Gel |
| MC % | 3% | 4% | 5% | 6% | 7% | 8% | 9% |

TABLE 2

| Citric | | | acid % | | | | |
|---|---|---|---|---|---|---|---|
| 4% | Gel | Gel | Gel | Gel | | | |
| 3% | Gel | Gel | Gel | Gel | | | |
| 2% | Gel | | Gel | | | | |
| 1% | Not | Gel | Gel | | | | |
| 0.5% | Not | Not | Gel | | | | |
| 0.3% | | Not | Gel | | | | |
| 0.1% | | | Not | Gel | | | |
| 0 | | Not | Gel | Gel | Gel | Gel | Gel |
| MC % | 3% | 4% | 5% | 6% | 7% | 8% | 9% |

EXAMPLE 2

A series of sample solutions were prepared similar to those in Example 1, with different methylcellulose and citric acid concentrations. Benzoic acid was added to these samples as a preservative with weight concentration of 0.2%, and all the solutions were adjusted to pH 4.0±0.1 by NaOH. The test was similar to that in Example 1 except that a 37° C. water bath was used instead of an oven, and the samples were removed from the water bath and held at room temperature for the inversion tests which were done for 5-10 seconds instead of 2 minutes because of the reduced testing temperature. The result is shown in Table 3.

TABLE 3

| MC % | Citric acid % | 10 minutes | 20 minutes | 30 minutes | 1 hours | 2 hours | overnight |
|---|---|---|---|---|---|---|---|
| 1% | 0.5% | | | | | | No |
| | 1.0% | | | | | | No |
| | 2.0% | | | | | | No |
| 2% | 0.5% | | | | | | No |
| | 1.0% | | | | | | No |
| | 2.0% | | | | | | Gel |
| 3% | 0.5% | | | | | | Gel |
| | 1.0% | | | | | | Gel |
| | 2.0% | | | | | almost | Gel |
| 4% | 0.5% | | | | | almost | Gel |
| | 1.0% | | | | almost | Gel | |
| | 2.0% | almost | Gel | | | | |
| 5% | 0.5% | | almost | Gel | | | |
| | 1.0% | almost | Gel | | | | |
| | 2.0% | Gel | | | | | |

EXAMPLE 3

A series of sample solutions were prepared similar to those in Example 1, with different methylcellulose and citric acid concentrations. METHOCEL A4C methylcellulose (Dow Chemical) was used for these experiments in de-ionized water containing benzoic acid as a preservative at a weight concentration 0.2%. Solutions were prepared with differing amounts of citric acid by first dispersing the methylcellulose in hot water between about 50-90° C. and then adding cold water to dissolve the methylcellulose. METHOCEL A4C methylcellulose has a viscosity of 400 mPa·s measured at 2 weight percent concentration in water at 20° C. All the solutions were adjusted to pH 4.00±0.25 by NaOH. A 37° C. water bath was used as in Example 2. Samples were inverted for 5-10 seconds to observe flow behavior. The results are shown in Table 4.

TABLE 4

| MC % | Citric acid % | 10 minutes | 35 minutes | 1 hours | 3 hours | 7 hours | overnight |
|---|---|---|---|---|---|---|---|
| 3% | 0.5% | | | | | | |
| | 1.0% | | | | | | |
| | 2.0% | | | | Gel | | |
| 4% | 0.5% | | | | | | Gel |
| | 1.0% | | | Gel | | | |
| | 2.0% | | Gel | | | | |

The preceding examples show the invention to be effective in gelling at the desired temperature range. Such a composition is useful in delivering other desirable compounds to the body and for soft tissue replacement.

As will be appreciated by those skilled in the art, changes and variations to the invention are considered to be within the ability of those skilled in the art. Examples of such changes are contained in the patents identified above, each of which is incorporated herein by reference in its entirety to the extent it is consistent with this specification. Such changes and variations are intended by the inventors to be within the scope of the invention.

What is claimed is:

1. A thermo-gelling composition consisting essentially of: an aqueous solution with at least 3 wt % to about 10 wt % of methylcellulose, about 0.5 wt % to about 6 wt % of citric acid or salt thereof, water, and at least one treating agent wherein the wt % of both methylcellulose and citric acid of salt thereof is based on the amount of water.

2. The thermo-gelling composition according to claim 1, wherein said methylcellulose is present in a concentration between about 4 and about 10 weight percent.

3. The thermo-gelling composition according to claim 1, wherein said methylcellulose is present in a concentration between about 5 and about 7 weight percent.

4. The thermo-gelling composition according to claim 1, wherein said citric acid or salt thereof is present at a concentration of between about 1 wt. % and about 6 wt. %.

5. The thermo-gelling composition according to claim 1, wherein said composition gels within a period of two hours.

6. The thermo-gelling composition according to claim 5, wherein said composition gels within a period of about 30 minutes.

7. The thermo-gelling composition according to claim 1, wherein said composition gels at a temperature between about 25° C. and about 40° C.

8. The thermo-gelling composition according to claim 1, wherein said composition has a final pH ranging from 2 to 9.

9. The thermo-gelling composition according to claim 1, wherein said composition when applied to a body forms a soft tissue replacement, or provides mechanical support or barrier functionality.

10. The thermo-gelling composition according to claim 1, wherein said composition further includes effective amounts of other ingredients selected from the group consisting of pH adjusters, tonicity adjusters, viscosity adjusters, polymeric thickeners, preservatives, antioxidants, and combinations thereof.

11. The thermo-gelling composition of claim 1, wherein said treating agent is selected from the group consisting of medicinal agents, cosmetic agents, moisturizers, adjuvants, nutritional agents, other ingredients and combinations thereof.

12. The thermo-gelling composition of claim 1, wherein said treating agent is a medicinal agent selected from the group consisting of agents for treating infection and menstruation disorders, agents for treating cardiovascular conditions, agents for treating internal conditions, agents for treating mental health conditions, anti-inflammatory agents, chemotherapeutic agents, cardiac tonics, expectorants, oral antiseptics, enzymes, birth control agents, ophthalmic treating agents and combinations thereof.

13. A therapeutic delivery medium consisting essentially of: a colloidal solution of water and at least 3 wt % to about 10 wt % of methylcellulose, about 0.5 wt % to about 6 wt % of citric acid or salt thereof, an effective amount of one or more treating agents wherein the wt % of both methylcellulose and citric acid of salt thereof is based on the amount of water, and said composition gels at a temperature between about 25° C. and about 40° C.

14. The therapeutic delivery medium according to claim 13, wherein said colloidal solution gels at a temperature between about 35° C. and about 39° C.

15. The therapeutic delivery medium according to claim 13, wherein said treating agent is a medicinal agent selected from the group consisting of agents for treating infection and menstruation disorders, agents for treating cardiovascular conditions, ophthalmic treating agents, anti-inflammatory agents, chemotherapeutic agents, birth control agents, cardiac tonics, expectorants, proteins, peptides, enzymes, hormones, and combinations thereof.

16. The therapeutic delivery medium according to claim 13, wherein said treating agent is a medicinal agent and is delivered in a controlled release manner.

17. The therapeutic delivery medium according to claim 13, wherein said treating agent is a medicinal agent and is delivered either topically or subcutaneously.

18. The therapeutic delivery medium according to claim 13, wherein said treating agent is a medicinal agent adapted to be delivered to a bodily mucosal surface location selected from the group consisting of vaginal, rectal, oral, ophthalmic, and nasal locations.

19. A drug delivery medium consisting essentially of: a thermo-gelling colloidal solution of water and at least 3 wt % to about 10 wt % of methylcellulose, about 0.5 wt % to about 6 wt % of citric acid or salt thereof, an effective amount of one or more medicinal agents, and said colloidal solution gels at a temperature between about 25° C. and about 40° C., enabling a sustained, controlled-release of said medicinal agent wherein the wt % of both methylcellulose and citric acid of salt thereof is based on the amount of water.

* * * * *

UNITED STATES PATENT AND TRADEMARK OFFICE
CERTIFICATE OF CORRECTION

PATENT NO. : 7,658,947 B2  Page 1 of 1
APPLICATION NO. : 10/877855
DATED : February 9, 2010
INVENTOR(S) : Huang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1112 days.

Signed and Sealed this

Thirtieth Day of November, 2010

David J. Kappos
*Director of the United States Patent and Trademark Office*